United States Patent [19]

Stapp

[11] Patent Number: 4,939,293

[45] Date of Patent: Jul. 3, 1990

[54] SULFONATED PHENOLIC MATERIAL AND ITS USE IN POST PRIMARY OIL RECOVERY

[75] Inventor: Paul R. Stapp, Bartlesville, Okla.

[73] Assignee: Phillips Petroleum Company, Bartlesville, Okla.

[21] Appl. No.: 910,560

[22] Filed: Sep. 22, 1986

Related U.S. Application Data

[62] Division of Ser. No. 632,936, Jul. 20, 1984, Pat. No. 4,632,786, which is a division of Ser. No. 382,042, May 25, 1982, Pat. No. 4,469,604.

[51] Int. Cl.$^5$ ............................................. C07C 143/44
[52] U.S. Cl. ..................................... 562/108; 562/110
[58] Field of Search ....................... 260/512 R, 512 C; 562/108, 110

[56] References Cited

U.S. PATENT DOCUMENTS 4,172,498 10/1979 Kalfoglou ...................... 252/8.55 D

OTHER PUBLICATIONS

Shearing et al., J. Chem. Soc., 1937, pp. 1348–1351.

Primary Examiner—Nicky Chan
Attorney, Agent, or Firm—J. E. Phillips

[57] ABSTRACT

Sulfonated phenolic compounds as well as sulfomethylated phenolic compounds, surfactant systems containing such compound and the use of such surfactant systems in post primary oil recovery are disclosed.

11 Claims, No Drawings

SULFONATED PHENOLIC MATERIAL AND ITS USE IN POST PRIMARY OIL RECOVERY

This application is a division of application Ser. No. 632,936, filed Jul. 20, 1984, now U.S. Pat. No. 4,632,786, which is a division of application Ser. No. 382,042, filed May 25, 1982, now U.S. Pat. No. 4,469,604.

This invention relates to new chemical compounds. In another aspect, this invention relates to a new surfactant system. In still another aspect, this invention relates to post primary oil recovery employing a new surfactant system.

BACKGROUND OF THE INVENTION

Water flooding and surfactant flooding are processes well known in the art to recover the vast quantities of oil which remain in the formation after primary oil recovery operations. Designing new surfactant systems of high oil recovery efficiency and good phase stability remains a goal in this technology.

The Invention

It is one object of this invention to provide a new chemical composition useful in oil recovery.

Another object of this invention is to provide a process for the production of such a new chemical composition which is inexpensive and employs readily available starting materials.

A further object of this invention is the provision of a surfactant system useful in surfactant flooding. Particularly the surfactant system should be useful in environments comprising hard brines.

Yet another object of this invention is to provide an oil recovery process using the surfactant system of this invention.

These and other objects, advantages, details, features and embodiments of this invention will become apparent to those skilled in the art from the following detailed description of the invention and the appended claims.

In accordance with this invention, a new chemical composition or respectively a mixture of new chemical compositions is provided which can be broadly characterized as a sulfonated alkyl substituted phenolic material. It has been found that such compositions, or mixtures of such compositions, are useful surfactants in post primary oil recovery.

Sulfonation Reaction

In accordance with a first embodiment of this invention, a process to produce the sulfonated phenolic material of this invention is provided. This process is characterized by a reaction between one or more alkyl or alkenyl substituted phenolic compounds in either a sulfonation reaction or a sulfomethylation reaction.

In both variations of this process embodiment the starting material for the sulfonation reaction, or respectively the sulfomethylation reaction, is a phenolic material which can be broadly characterized as an alkyl substituted hydroxyaryl compound having an unsubstituted aromatic carbon atom in an ortho position with respect to the phenolic hydroxyl substitution. The starting material used can also be characterized by the formula

wherein Ar is an aromatic hydrocarbyl moiety having the —OH and the —X in ortho position to each other, so that —OH and —X are attached to neighboring aromatic carbons, which aromatic hydrocarbyl moiety may be further substituted by one or more —OH groups and/or hydrocarbyl substituents, wherein —X is hydrogen, wherein R is an alkyl or alkenyl radical having 1 to 30 carbon atoms with the proviso that at least one radical R has 6 to 30 carbon atoms, wherein n is 1, 2 or 3, and wherein the total number of carbon atoms in all n radicals R and in the aromatic moiety Ar together is 12 to about 40, with the further proviso that the total number of phenolic —OH groups in the molecule is preferably 1 to 3 and most preferably 1 or 2.

This phenolic starting material carrying a sulfonatable or sulfomethylatable aromatic C—H configuration is subjected to one of the following chemical reactions.

Sulfonation

The sulfonation of the alkyl substituted phenolic material can be carried out in a variety of ways which are basically known in the art. Among the sulfonation agents that can be used are fuming sulfuric acid, $SO_3$, a solution of $SO_3$ in $SO_2$, concentrated sulfuric acid and the like. The sulfonation reaction is generally carried out utilizing a slight excess of the sulfonating agent. The sulfonating conditions include temperatures in the range of $-30°$ to $150°$ C. and reaction times in the range of a few minutes to several hours. The pressure for the sulfonation reaction is generally such that the ingredients remain in the liquid phase under the utilized temperature conditions.

The sulfonated alkyl substituted phenolic material obtained in the above described reaction can be separated from the reaction mixture. The sulfonic acid produced in the sulfonation step is generally neutralized prior to or following the above mentioned separation step. It is, however, also within the scope of this invention to employ the sulfonation mixture after neutralization as such in post primary oil recovery to be described in the following.

The neutralization of the sulfonic acid formed in the sulfonation of the phenolic starting material is advantageously carried out by contacting the sulfonated alkyl substituted phenolic compound with a base. Among the bases useful for this neutralization step the alkali metal oxides and hydroxides, and in particular the sodium and potassium oxides and hydroxides, and the ammonium and amine bases are preferred. The ammonium and amine bases can be broadly characterized by the formula

with or without water, wherein $R^{(1)}$ is hydrogen, alkyl having 1 to 3 carbon atoms, and hydroxy alkyl with 2 or 3 carbon atoms, preferably 2 carbon atoms.

The base employed in the neutralization reaction is usually used in a slight stoichiometric excess. The neutralization step is carried out at a temperature generally in the range of 20° to 100° C. while the pressure is maintained to keep the reacting mass essentially in the liquid phase. The neutralization reaction is generally terminated in a few minutes.

It is within the scope of this invention and under certain circumstances it is preferred to use the sulfonation reaction product as such without prior separation in the neutralization step and to use a neutralized solution as such in post primary oil recovery without prior separation step.

The sulfonation reaction and subsequent neutralization results in a sulfonate surfactant which is particularly desirable in surfactant flooding operations for post primary oil recovery. The chemical formula of the sulfonate salt is

wherein R, Ar are as defined above and wherein $Y^{(1)}$ is —$SO_3$—Cat wherein Cat stands for —Na, —K, —$NHR_3^{(1)}$ with $R^{(1)}$ having the same meaning as above.

Sulfomethylation

In accordance with a second variation of this embodiment of this invention, novel chemical compositions are produced by a sulfomethylation reaction of the alkyl or alkenyl substituted phenolic starting materials defined above. This sulfomethylation reaction involves the reaction between the phenolic starting material, formaldehyde and a sulfonating agent. The presently preferred sulfonating agents are alkali metal sulfites or bisulfites, ammonium sulfite or ammonium bisulfite, or amine salts characterized by the formula

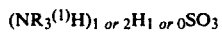

wherein $R^{(1)}$ has the same meaning as defined above. The formaldehyde as well as the sulfite compounds are employed in this sulfomethylation reaction approximately in stoichiometric quantities, i.e., one molecule of each compound is used per phenolic hydroxyl group of the phenolic starting material. The formaldehyde and the sulfite can be used in slight excess. The sulfomethylation reaction is carried out under temperature in the range of 0° to 150° C. while the pressure is maintained high enough to keep the reactants in the liquid state. The time for the sulfomethylation reaction will generally be in the range of a few minutes to 24 hours.

The sulfomethylated product produced in accordance with this invention is believed to constitute a novel composition of matter.

The Compounds of This Invention

Both the sulfonated and the sulfomethylated phenolic compounds are believed to be novel compositions of matter. The preparation of these compounds has been described above.

The novel compositions of this invention can be generally characterized by the following formula

wherein R, Ar and n have the meaning as defined above and Z is selected from the group of radicals consisting of —$SO_3$—Cat and —$CH_2$—$SO_3$—Cat, with Cat having the same meaning as described and defined above. The radical Z and the —OH group are both attached to the aromatic ring structure Ar and are in ortho position relative to each other. The total number of carbon atoms in all n radicals R and the aromatic moiety Ar together is in the range of 12 to about 40.

The total number of phenolic —OH groups in the molecule will be 1 to 3 preferably 1 or 2; the molecule will usually not contain more than three sulfonate substituents, and preferably will have 1 or 2 of such sulfonate substituents. Particularly preferred are compounds which have just one sulfonate substituent.

In the following, some examples of phenolic structures are given. In these examples, the structures refer to both the starting material phenols as used in the process for producing the novel sulfonated or methyl sulfonated compounds as well as the final products. X, Y and Z have the meanings as defined above and X, being hydrogen, refers to the starting phenolic material while the substituents Y and, respectively, Z refer to the sulfonated or respectively methyl sulfonated products. Examples of the phenolic molecule structure are given in the following:

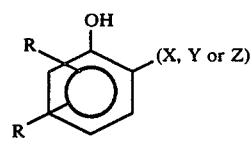

mono- or dialkyl phenols and their sulfonated or sulfomethylated counterparts;

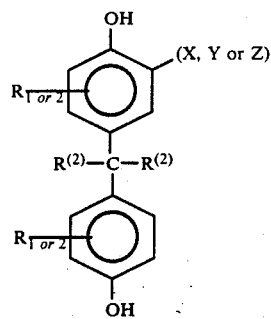

alkylated bisphenols and their sulfonated and sulfomethylated counterparts; $R^{(2)}$ is H or $CH_3$

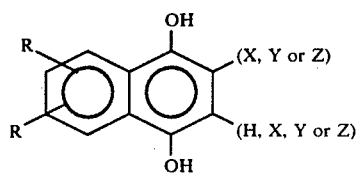

mono- and dialkyl 4-hydroxy naphthols and their sulfonated and sulfomethylated counterparts.

Surfactant System

A further embodiment of this invention is a surfactant system. This system comprises brine, a sulfonated or sulfomethylated phenolic composition as defined above and a cosurfactant.

The surfactant system of this invention optionally contains a protective agent. Water is used containing a certain quantity of sodium chloride for practical reasons. Typical and preferred compositions of a surfactant system of this invention are shown in the following table.

TABLE I

| INGREDIENT | BROAD RANGE | PREFERRED RANGE |
| --- | --- | --- |
| Water (parts by weight) | 100 | 100 |
| Phenolic Sulfonate* (active parts by weight) | 0.1–15 | 1–12 |
| Cosurfactant (parts by weight) | 0.05–15 | 1–7 |
| Protective Agent (optional) (parts by weight) | 0.01–3 | 0.05–2 |
| NaCl (parts by weight) | 0.1–10 | 0.1–8 |

*The ranges for the active sulfonate in parts by weight. The "active" value is readily determined by multiplying parts by weight used and the percentage of active ingredients in the product.

The cosurfactant used in the surfactant system of this invention is preferably one that is selected from the group consisting of organonitriles and alcohols. The nitriles can be broadly characterized as organonitriles having 1 to 3 —CN groups attached to carbon atoms in compounds containing a total of 2 to 40 carbon atoms and up to 4 oxygen and/or sulfur atoms and up to 4 additional nitrogen atoms. The preferred nitriles are acetonitrile, propionitrile, butyronitrile, α-methyleneglutaronitrile, tridecanenitrile, benzonitrile, phenylacetonitrile, acrylonitrile, methacrylonitrile, vinylacetonitrile, succinonitrile, 1,3-dicyanopropene, 1,3-dicyano-3-butene, tris(cyanoethyl)methane, 1,1-dicyanoethane and mixtures thereof. The preferred nitrile when used is acrylonitrile. The alcohols contemplated as cosurfactants in accordance with this invention include alcohols having 3 to 12 carbon atoms, preferably 3 to 8 carbon atoms. Examples of useful alcohols which can be employed as cosurfactants include isopropanol, 1-butanol, isoamyl alcohol, isobutyl alcohol, hexanol, octanol, dodecanol, heptanol, decanol and mixtures thereof. The preferred alcohol cosurfactant is isoamyl alcohol.

Oil Recovery Process

A further embodiment of this invention resides in an oil recovery process. This process involves generally the conventional steps of post primary oil recovery and distinguishes over the known procedures primarily in the use of the novel compounds defined above and in the surfactant system employing these novel compounds.

Preflush

It is optional, although not necessary, to carry out a preflush step preceding the further oil recovery operation. Such preflush operations are known in the art. Generally, a brine compatible with the surfactant system is injected via at least one injection well into the subterranean formation. Such a brine typically contains 2000–50,000 ppm salts, predominantly sodium chloride. Preferably a brine solution as utilized in the production of the surfactant system is also used in this preflush step.

The quantity of the preflush employed will generally be in a range of about 0.01 to 2, preferably 0.25 to 1 pore volume, based on the total pore volume of the formation or reservoir subjected to the recovery.

Surfactant Flooding

After the optional preflush step the surfactant system of this invention is injected into the reservoir via at least one injection well. The surfactant system is injected in an amount usually in the range of about 0.001 to 1.0, preferably 0.01 to 0.25 pore volume based again on the pore volume of the total treated and produced formation.

The preferred operation makes use of the surfactant system in a manner that a multiphase system including at least one microemulsion phase is formed in the formation. Usually the surfactant system contains as the main ingredients water, the surfactant including the sulfonated or sulfomethylated phenolic compound and the cosurfactant. These ingredients are thoroughly mixed and then introduced into the formation via one or more injection wells. However, the in-situ formation of a microemulsion in the formation, e.g. by simultaneous but unmixed injection or by alternating the injection of surfactant and cosurfactant is also within the scope of this invention.

Generally, the microemulsion is formed in the reservoir after the surfactant system is injected as a solution containing surfactant and cosurfactant in brine.

The present invention can be utilized for a variety of subterranean reservoirs. The invention is, however, particularly preferred in reservoirs containing hard brine connate water. Such hard brines are characterized by a high content of $Mg^{++}$ and $Ca^{++}$ ions in the reservoir water. Typical hard brines contain more than 100 ppm of $Ca^{++}$ and/or $Mg^{++}$. The concentration range of these ions extends to 10,000 ppm, usually to 1000 ppm.

If additional protective agents are employed in the surfactant system of this invention, they are utilized in the quantities shown above in addition to the novel compositions of this invention. Examples for such protecting agents are polyethoxylated fatty alcohols and polyethoxylated alkylphenols. In addition, the sodium salts of sulfated polyethoxylated fatty alcohols and polyethoxylated alkylphenols are known in the art to function as protective agents.

Mobility Buffer

Following the surfactant slug it is presently preferred, although not necessary, to inject a mobility buffer solution into the reservoir. This buffer helps prevent fingering and enhances the efficiency of the oil recovery. Buffer solutions are aqueous solutions of polymeric viscosifiers or other thickening agents. Examples of useful mobility buffers are aqueous fluids containing mobility reducing agents such as high molecular weight partially hydrolyzed polyacrylamides, biopolysaccharides, soluble cellulose ethers and the like. The mobility buffer comprises 50 to 20,000, preferably 200 to 5,000 ppm of the mobility reducing agent in the fluid.

The concentration of the thickening agent in the mobility buffer fluid can remain constant over the injection period or the mobility buffer slug can be "graded", i.e., the viscosifier concentration starts out at a relatively high level at the beginning of the injection and the concentration tapers off toward the end of the injection. As an example, the aqueous mobility buffer slug can start with a concentration of 2500 ppm of polyacrylamide and be graded back by continuous dilution to 250 ppm of polyacrylamide. The "grading" of mobility buffer fluids is well-known in the art.

The following examples are intended to further illustrate the invention without unduly limiting the scope thereof.

EXAMPLE I

This example describes the sulfomethylation of p-dodecylphenol.

A charge of 32.8 g (0.125 mol) of p-dodecylphenol, 63.0 g (0.50 mol) of anhydrous sodium sulfite, 250 mL of water and 20 g (0.250 mol) of 37 weight percent aqueous formaldehyde was placed in a 500 mL round-bottomed flask equipped with $N_2$ inlet tube, magnetic stirring bar and water-cooled reflux condenser. The mixture was boiled at reflux under a nitrogen atmosphere for a period of 20 hours. During this period, the reaction mixture became a yellow pasty material suspended in water but toward the end of the reflux period the reaction mass appeared to be a white crystalline suspension. The mixture was acidified to a pH of 6 with dilute aqueous sulfuric acid and the precipitate was collected by filtration. This product was taken up in isopropanol and the solution was filtered to remove insoluble matter. The isopropanol filtrate was stripped of volatiles on a rotary evaporator to leave 36.3 g of a white crystalline residue. Continuous extraction of this material with n-butanol yielded no additional product. An elemental analysis of the product gave the following results:

| % C | 66.9 |
|---|---|
| % H | 9.24 |
| % S | 5.06 |

Theoretical percentage for sulfur is 8.47% in 5-dodecyl-2-hydroxy-alphatoluenesulfonate. The above product is about 60% pure based on percent sulfur found in the above analysis. Presumably, the major component in the white crystalline residue is sodium 5-dodecyl-2-hydroxy-alphatoluenesulfonate.

EXAMPLE II

This example describes the sulfomethylation of p-nonylphenol.

A charge of 110 g (0.5 mol) p-nonylphenol and 500 mL of an aqueous mixture containing 126 g (1.0 mol) anhydrous sodium sulfite and 26.5 g (0.25 mol) anhydrous sodium carbonate was placed in a 1-liter round-bottomed flask equipped with magnetic stirring bar and watercooled reflux condenser. This mixture was stirred vigorously as 60.5 g (22.5 g, 0.75 mol $CH_2O$) of 37 weight percent aqueous formaldehyde was added in a dropwise fashion over a 30 minute period. The stirred mixture was then boiled at reflux for about 14 hours. The milky gelatinous mixture was then cooled to room temperature, acidified to a pH of 6 with aqueous sulfuric acid and extracted with chloroform. The chloroform phase was separated and stripped on a rotary evaporator to give a white crystalline solid which weighed 118.7 g. By hyamine titration (sulfonate determination) a value of 2.03 meq/g was determined. Theory for sodium 5-nonyl-2-hydroxy-alpha-toluenesulfonate (Formula Weight 336) is 2.98 meq/g. Based on these equivalent weight values the reaction product was about 68% pure.

The following experimental procedure was used to condition sandstone cores for surfactant flood runs to demonstrate the effectiveness of the inventive material in tertiary oil recovery.

Experimental

General

Berea sandstone cores of the desired length and 3 inches in diameter were dried under vacuum for 24 hours at 250° F. Polycarbonate disc end plates with centrally located ⅛" threaded openings were secured to each end of the core with epoxy adhesive before applying an epoxy coating to the outside surface of the core. The epoxy coating material was formulated by mixing 550 g of a commercially available epoxy resin, 50 g of a suitable activator and 140 g diatomaceous earth. This mixture was stirred until smooth before applying to the surface of the core. The cores were rotated continuously as the epoxy mixture was applied with a 2" paint brush. Four gauze strips measuring 2"×12" were applied to the core in the following manner: a first gauze strip was applied to the core and covered with epoxy as the core was rotated; the remaining three strips were then individually incorporated in a similar manner. The core coating was cured over a period of about 4 hours at ambient temperature as the core was rotated. One-eighth inch male connector fittings were placed on each end of the core and pipe plug caps were put on the core.

The core was weighed to determine the dry weight before being saturated with brine of the desired concentration. A vacuum of about 1 mm was pulled on the core before saturating the core with approximately 500 mL of brine. After saturation, approximately 100 to 200 mL of brine were pumped through the core before determining the original permeability to water. A 1 mL portion of effluent brine was collected from the saturated core and thereafter during a period of one minute, the volume of additional effluent collected and the pressure in psi were recorded. With these values the original permeability to water, e.g., on the order of 3.2 mL/min at 43 psi could be recorded. The pore volume of the core was calculated by the relationship:

$$\frac{\text{Brine-Saturated Core Wt (g)} - \text{Dry Core Wt (g)}}{\text{Brine Density (g/mL)}} =$$

Core Pore Volume (mL)

The brine-saturated core was oil flooded in the conventional manner until oil break-through became detectable by the presence of alternate globules of oil and water in the effluent line. The oil flood was carried out to completion by the 24 hour recycling of oil through the core to remove all of the displaceable water. The total water displaced, i.e., water displaced at the point of oil break-through and water displaced by the 24 hour recycle procedure was recorded as water displaced by oil flood. If desired, oil permeability was determined in a manner analogous to that used above for establishing original permeability to water. Prior to waterflood, the effluent line was air blown to remove oil.

The oil-flooded core was waterflooded in the conventional manner until water break-through became detectable by the presence of alternate globules of oil and water in the effluent line. The waterflood was carried to completion by the 24 hour recycling of water through the core to remove all of the displaceable oil. The total oil displaced, i.e., oil displaced at the point of water break-through and oil displaced by the 24 hour recycle procedure was recorded as oil displaced by waterflood. If desired, water permeability after waterflood can be determined in a manner analogous to that used above for original permeability to water. The residual oil volume remaining in the core was calculated by subtracting the oil volume displaced by the waterflood from the water volume displaced by the oilflood. At this point, the core simulated an oil reservoir which had been exhaustively waterflooded. Cores were routinely conditioned in this manner prior to carrying out surfactant flood tests.

The following example shows the effectiveness of the sulfomethylated nonylphenol composition as a surfactant in recovering oil from waterwet Berea sandstone cores.

EXAMPLE III

Surfactant flooding of a waterwet Berea sandstone core was carried out in the conventional manner, i.e., sequential injection of surfactant slug, mobility buffer and drive water. The preparation of the surfactant is described in Example II. The core run result is shown in Table II.

TABLE II

| Run No. | % PV Surfactant Slug | Added Cosurfactant | % Tertiary Recovery | Salinity Wt. % NaCl |
|---|---|---|---|---|
| 1 | 25 | IAA* | 81.8 | 3.0 |

*IAA represents isoamyl alcohol (3.0 wt. % of the surfactant slug).

Referring to Table II, it is evident that the sulfomethylated derivative of p-nonylphenol is an effective surfactant for recovering waterflood residual oil from a waterwet Berea sandstone core at a salinity of 3.0 weight percent NaCl.

EXAMPLE IV

This example describes the sulfonation of p-dodecylphenol and the use of the reaction product as a surfactant in recovery of waterflood residual oil from Berea sandstone cores.

A charge of 100 g (0.381 mol) p-dodecylphenol was placed in a 400 mL beaker equipped with a magnetic stirring bar and placed on a stirrer hot-plate. The phenol was stirred at ambient temperature during the slow addition of 30 mL fuming sulfuric acid. After the heat of reaction had subsided, the stirred reaction mass was warmed briefly before being cooled to ambient temperature and stirred an additional 14 hours. The reaction mixture was neutralized with aqueous sodium hydroxide, transferred to a separatory funnel and extracted successively with 100 mL portions of hexane. The hexane extracts were combined and concentrated on a rotary evaporator to a viscous reddish-brown colored liquid. The water phase was concentrated and dried to a solid residue in a rotary evaporator. This residue was further dried by the addition of toluene and stripping. This solid was partially soluble in acetone: the acetone-insoluble portion was filtered off and treated with ethanol. The ethanol-insoluble matter was separated by filtration and the ethanol soluble material was isolated by stripping the ethanol to give a residual light yellow powder which weighed about 24.5 g. An infrared spectrum analysis of this material verified the presence of sulfonate groups. The active sulfonate surfactant species in this material was presumably sodium dodecylphenol sulfonate.

EXAMPLE V

Surfactant flooding of a waterwet Berea core containing waterflood residual oil was carried out in the conventional manner, i.e., sequential injection of preflush slug, surfactant slug and mobility buffer. The preflush slug was a 50% PV solution containing 2.0 weight percent sodium chloride and 2.07 weight percent isoamyl alcohol. The surfactant slug was a 10% PV solution containing 3.12 weight percent of the light yellow powder reaction product (sodium p-dodecylphenol sulfonate) made in Example IV, 2.07 weight percent isoamyl alcohol, 2.0 weight percent sodium chloride and 1750 ppm soluble calcium ion. The mobility buffer slug was a 43 centipoise solution of Betz Hi-Vis polyacrylamide in Arkansas-Burbank river water (<500 ppm total dissolved solids) graded back logarithmically with Arkansas-Burbank water. The core run result is summarized in Table III.

TABLE III

| Run No. | % PV Surfactant Slug | Added Cosurfactant | % Tertiary Recovery | Salinity Wt. % NaCl |
|---|---|---|---|---|
| 2 | 10 | IAA* | 61 | 2.0 |

*IAA represents isoamyl alcohol.

Referring to Table III, it is evident that the sulfonated derivative of p-dodecylphenol is an effective surfactant for recovering waterflood residual oil from a Berea sandstone core.

EXAMPLE VI

This example demonstrates that an inventive anionic surfactant such as the sulfomethylated derivative of dodecylphenol is partitioned mostly into the aqueous phase of a heptane/isobutyl alcohol/hard brine system wherein the brine contains a significant concentration of $Ca^{++}$. Control runs contained a commercially available sodium petroleum sulfonate (Witco Chem. Co. TRS10-410) and it was observed that the petroleum sulfonate surfactant was partitioned almost entirely into the heptane phase of said heptane/isobutyl alcohol/hard brine system.

A mixture was prepared by combining 180 mL of distilled water, 1.9 g anhydrous $Na_2CO_3$, 6.9 mL isobutyl alcohol and 5.4 g (8:59 mmols, 60.1% active basis) of sulfomethylated dodecylphenol. To this mixture was added 4.3 mL of 1M $CaCl_2$ solution (4.3 mmols $Ca^{++}$). This solution was equilibrated with heptane (50 mL) by stirring for about 2 hours at ambient temperature and then allowed to stand for about 48 hours to permit the organic and aqueous phases to separate.

Analysis showed that 76.1% of the inventive sulfomethylated dodecylphenol was present in the aqueous phase and the remaining sulfonate (23.9%) was solubilized into the heptane phase.

For the control runs, the procedure was as follows:
C-5:

A charge of 100 g (0.0861 mol/1.) of petroleum sulfonate, active basis) of deoiled TRS10-410 solution and 25.2 g of 0.340M $CaCl_2$ solution (8.61 mmols of $Ca^{++}$) was placed in a 250 mL Erlenmeyer flask. A white precipitate formed immediately on mixing and the mixture was stirred overnight at ambient temperature. A 20 mL portion of heptane and a 3 mL portion of isobutyl alcohol was added to the mixture and stirring was continued for two days.

The stirring was stopped and after standing at ambient temperature for 6 hours, two transparent phases formed and a very small amount of white solid was evident at the interface. A sample of the aqueous phase on analysis showed the presence of 0.0014 meq of sulfonate/g of aqueous phase. Since the original deoiled solution of TRS10-410 contained 0.086 meq of petroleum sulfonate, it is evident that about 1.6% of the sulfonate was present in the aqueous phase and the remaining 98.4% of the sulfonate was solubilized into the heptane phase presumably as the relatively oil-soluble calcium salt form.

C-1:
The procedure was essentially the same as C-5 except 12.6 g (4.3 mmols $Ca^{++}$) of a 0.340M $CaCl_2$ solution was used.

A sample of the aqueous phase on analysis showed the presence of 0.0016 meq of sulfonate/g of aqueous phase. Thus, it is evident that about 1.8% of the sulfonate was present in the aqueous phase and the remaining 98.2% of the petroleum sulfonate was solubilized into the heptane phase presumably as the relatively oil-soluble calcium salt form.

C-2:
This procedure was essentially identical to C-5 except the stock solution of deoiled TRS10-410 petroleum sulfonate was prepared in 1 weight percent aqueous sodium chloride solution rather than distilled water.

Analysis showed 1.4% of the sulfonate in the aqueous phase and the remaining 98.6% of the petroleum sulfonate was solubilized into the heptane phase presumably as the relatively oil-soluble calcium salt form.

C-3:
This procedure was similar to that used in C-5 except that no divalent cations such as $Ca^{++}$ or $Mg^{++}$ were present.

A sample of the aqueous phase (after the equilibrium of the TRS10-410 stock solution with 20 mL of heptane and 3 mL isobutyl alcohol) on analysis showed the presence of 0.078 meq of sulfonate/g of aqueous phase. Thus, it is evident that approximately 90.6% of the sulfonate was present in the aqueous phase and 9.4% of the relatively oil-insoluble sodium salt form of the petroleum sulfonate was in the heptane phase.

C-4:
This procedure was essentially the same as C-5 except 6.3 g (2.15 mmols $Ca^{++}$) of a 0.340M $CaCl_2$ solution was used.

A sample of the aqueous phase on analysis showed the presence of 0.0027 meq of sulfonate/g of aqueous phase. Thus, it is evident that about 3.1% of the sulfonate was present in the aqueous phase and the remaining 96.9% of the petroleum sulfonate was solubilized into the heptane phase presumably as the relatively oil-soluble calcium salt form.

C-6:
This procedure was essentially the same as C-5 above except 35 g of a 0.246M $MgCl_2$ solution (8.61 mmols $Mg^{++}$) was used.

A sample of the aqueous phase on analysis showed the presence of 0.0012 meq of sulfonate/g of aqueous phase. Thus, it is evident that about 1.4% of the sulfonate was present in the aqueous phase and the remaining 98.6% of the petroleum sulfonate was solubilized into the heptane phase presumably as the relatively oil-soluble magnesium salt form.

C-7:
This procedure was essentially the same as C-6 above except 17.5 g of a 0.246M $MgCl_2$ solution (4.3 mmols $Mg^{++}$) was used.

A sample of the aqueous phase on analysis showed the presence of 0.0019 meq of sulfonate/g of aqueous phase. Thus, it is evident that about 2.2% of the sulfonate was present in the aqueous phase and the remaining 97.8% of the petroleum sulfonate was solubilized into the heptane phase presumably as the relatively oil-soluble magnesium salt form. Results are summarized in Table IV.

TABLE IV

Partitioning of Surface Active Sulfonates in Heptane/Isobutyl Alcohol/Hard Brine Systems

| Run Type (C = Control | Sulfonate Used | mmols $Ca^{++}$ | mmols $Mg^{++}$ | % Sulfonate $H_2O$ Phase | % Sulfonate Heptane Phase |
|---|---|---|---|---|---|
| Invention | SMDP# | 4.3 | None | 76.1 | 23.9 |
| C-1 | TRS10-410[a] | 4.3 | None | 1.8 | 98.2 |
| C-2[b] | TRS10-410 | 4.3 | None | 1.4 | 98.6 |
| C-3[c] | TRS10-410 | None | None | 90.6 | 9.4 |
| C-4 | TRS10-410[a] | 2.15 | None | 3.1 | 96.9 |
| C-5 | TRS10-410[a] | 8.6 | None | 1.6 | 98.4 |
| C-6 | TRS10-410[a] | None | 8.6 | 1.4 | 98.6 |
| C-7 | TRS10-410[a] | None | 4.3 | 2.2 | 97.8 |

SMDP represents the inventive sulfomethylated dodecylphenol.
[a]A stock solution of deoiled TRS10-410 (Witco Chem. Co. petroleum sulfonate, sodium salt form; average equivalent weight 418) was prepared by combining 18 g of the deoiled sulfonate with 482 g distilled water. This solution contained approximately 8.6 mmols of sulfonate per 100 g portions used in each of the above equilibrations.
[b]The stock solution of deoiled TRS10-410 contained 1 wt. % NaCl.
[c]An 87.5 g portion rather than a 100 g portion of the deoiled TRS10-410 stock solution was used in this run.

Referring to the control run C-3, it is evident that equilibration of petroleum sulfonate (sodium salt form) in the system $H_2O$/heptane/isobutyl alcohol results in the majority of the petroleum sulfonate partitioning into the aqueous phase. Referring to the remaining control runs (C-1, C-2 and C-4 through C-7), it is evident that the addition of divalent cations such as $Ca^{++}$ or $Mg^{++}$ to the equilibration system results in the partitioning of the petroleum sulfonate into the heptane phase presumably as the relatively oil-soluble divalent cation salts form. In sharp contrast, the partitioning of the inventive sulfomethylated dodecylphenol (see Invention Run) in a $Ca^{++}$ containing system was distributed between into the aqueous phase and the heptane phase. Similar control runs (see C-1 and C-2) with comparable $Ca^{++}$ concentrations, showed partitioning of petroleum sulfonate mostly to the heptane phase rather than the aqueous phase.

Reasonable variations and modifications which will become apparent to those skilled in the art can be made from this invention without departing from the spirit and scope thereof.

That which is claimed is:

1. Process to produce sulfomethylated phenolic compounds comprising reacting a phenolic starting material comprising alkyl substituted hydroxy aromatic compounds having an unsubstituted aromatic carbon atom in an ortho position with respect to said phenolic starting material selected from the group consisting of alkyl phenols having the formula alkylated bisphenols having the formula

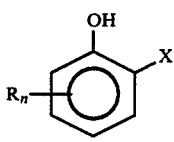

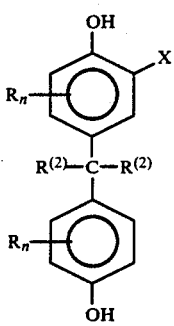

and, alkylated naphthols having the formula

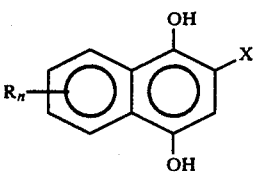

wherein, in each of the formulas above, R is alkyl or alkenyl having up to 30 carbon atoms, with the proviso that at least one radical R has 6 to 30 carbon atoms;

wherein, $R^{(2)}$ is H or $CH_3$;

wherein, n is the number 1 or 2; and wherein, X is hydrogen, with the further proviso that the total number of carbon atoms per molecule is 13 to about 40, with formaldehyde in the presence of a sulfonating agent to produce compounds selected from the group consisting of sulfomethylated alkyl phenols having the formula

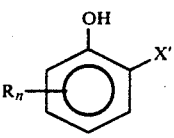

sulfomethylated alkyl bisphenols having the formula

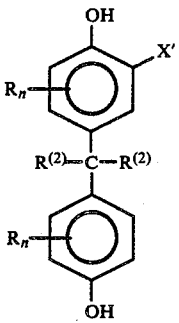

and, sulfomethylated alkylated naphthols having the formula

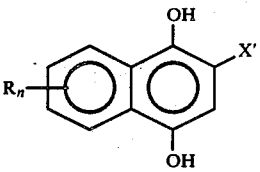

respectively, wherein, R, n, and $R^{(2)}$ have the same meaning as defined above; and wherein, X' is $CH_2$—$SO_3$—Cat, wherein Cat is selected from the group consisting of —Na, —K and —$NHR_3^{(1)}$ and wherein each of $R^{(1)}$ is selected from the group consisting of hydrogen, a alkyl radical having 1 to 3 carbon atoms and hydroxyalkyl with 2 or 3 carbon atoms.

2. Process in accordance with claim 1 wherein Cat is sodium.

3. A process in accordance with claim 1 wherein said sulfonating agent is selected from the group consisting of alkali metal sulfites or bisulfites, ammonium sulfite or ammonium bisulfite, or amine salts having the formula $(NR_3^{(1)}H)_nH_mSO_3$ wherein $R^{(1)}$ and n have the same meaning as defined in claim 1, and wherein m is the number 0 or 1.

4. Process in accordance with claim 1 wherein said phenolic starting material is a mixture of a plurality of phenolic compounds.

5. Process in accordance with claim 1 wherein said mixture of phenolic compounds is derived from by-product hydrocarbon process streams.

6. A process in accordance with claim 12 wherein said sulfonating agent is sodium sulfite.

7. A process in accordance with claim 1 wherein said phenolic starting material is said alkyl phenol having the formula

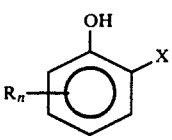

wherein R, n, and X have the same meaning as defined above.

8. A process in accordance with claim 1 wherein said phenolic starting material is said alkylated bisphenol having the formula

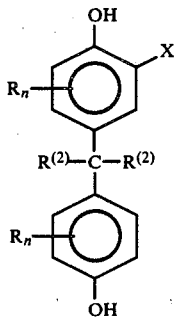

wherein R, n, X, and $R^{(2)}$ have the same meaning as defined above.

9. A process in accordance with claim 1 wherein said phenolic starting material is said alkylated naphthol having the formula

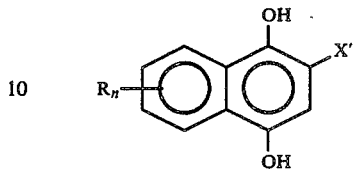

wherein R, n, and X have the same meaning as defined above.

10. A process in accordance with claim 7 wherein said alkyl phenol is p-dodecylphenol.

11. A process in accordance with claim 7 wherein said alkyl phenol is p-nonylphenol.

* * * * *

UNITED STATES PATENT AND TRADEMARK OFFICE
CERTIFICATE OF CORRECTION

PATENT NO. : 4,939,293

DATED : July 3, 1990

INVENTOR(S) : Paul R. Stapp, et al

It is certified that error appears in the above-identified patent and that said Letters Patent is hereby corrected as shown below:

On the title page item [75] should read, -- Paul R. Stapp and Jerry E. Pardue--.

Signed and Sealed this

Fifth Day of November, 1991

Attest:

HARRY F. MANBECK, JR.

*Attesting Officer*      *Commissioner of Patents and Trademarks*